US007223549B2

(12) United States Patent
Makarovskiy

(10) Patent No.: US 7,223,549 B2
(45) Date of Patent: *May 29, 2007

(54) COMPOSITIONS FOR IDENTIFICATION AND ISOLATION OF STEM CELLS

(75) Inventor: Andrew N. Makarovskiy, Mendon, MA (US)

(73) Assignee: Andrew N. Marakovskiy, Mendon, MA (US)

( * ) Notice: Subject to any disclaimer, the term of this patent is extended or adjusted under 35 U.S.C. 154(b) by 583 days.

This patent is subject to a terminal disclaimer.

(21) Appl. No.: 10/315,492

(22) Filed: Dec. 10, 2002

(65) Prior Publication Data

US 2003/0134338 A1    Jul. 17, 2003

Related U.S. Application Data

(63) Continuation of application No. 09/603,453, filed on Jun. 22, 2000, now Pat. No. 6,632,620.

(51) Int. Cl.
| | |
|---|---|
| *C07K 16/28* | (2006.01) |
| *G01N 33/563* | (2006.01) |
| *G01N 33/577* | (2006.01) |
| *G01N 33/533* | (2006.01) |
| *G01N 33/534* | (2006.01) |
| *G01N 33/535* | (2006.01) |
| *C07K 16/30* | (2006.01) |
| *C12N 5/20* | (2006.01) |
| *G01N 33/574* | (2006.01) |

(52) U.S. Cl. ............... 435/7.21; 435/7.23; 435/735; 435/21; 435/28; 435/69.1; 435/70.21; 435/330; 435/975; 436/512; 436/548; 436/172; 436/804; 530/387.3; 530/388.2; 530/388.8; 530/391.3; 530/391.7

(58) Field of Classification Search .............. 435/7.21, 435/7.23, 7.4, 7.95, 70.21, 451, 452, 330, 435/332, 334, 344, 7.5, 69.1, 21, 28, 975; 436/518, 519, 536, 548, 813, 512, 172, 804; 530/388.2, 388.22, 388.8, 828, 850, 387.3, 530/391.3, 391.7

See application file for complete search history.

(56) References Cited

U.S. PATENT DOCUMENTS

| | | | |
|---|---|---|---|
| 4,714,680 A | 12/1987 | Civin | |
| 5,061,620 A | 10/1991 | Tsukamoto et al. | |
| 5,087,570 A | 2/1992 | Weissman et al. | |
| 5,486,359 A | 1/1996 | Caplan et al. | |
| 5,548,065 A | 8/1996 | Lemischka | |
| 5,773,224 A | 6/1998 | Grandics et al. | |
| 5,789,246 A | 8/1998 | Reid et al. | |
| 5,861,313 A | 1/1999 | Pang et al. | |
| 6,258,939 B1 | 7/2001 | Reiter et al. | |
| 6,632,620 B1 * | 10/2003 | Makarovskiy | ............ 435/7.21 |

FOREIGN PATENT DOCUMENTS

| | | |
|---|---|---|
| WO | WO 92 14821 | 9/1992 |
| WO | WO 92/18643 | 10/1992 |
| WO | WO 92/22584 | 12/1992 |
| WO | WO 93/25216 | 12/1993 |
| WO | WO 96/15229 | 5/1996 |
| WO | WO 96/22693 | 8/1996 |
| WO | WO 96/40875 | 12/1996 |
| WO | WO 98/00523 | 1/1998 |
| WO | WO 98 40403 | 9/1998 |
| WO | WO 99/23205 | 5/1999 |
| WO | WO 99/61584 | 12/1999 |
| WO | WO 99/61587 | 12/1999 |

OTHER PUBLICATIONS

Kubota, et al., Clonogenic hepatoblasts, common precursors for hepatocytic and biliary lineages, are lacking classical major histocompatibility complex class I antigen, Proc. Natl. Acad. Sci. USA 97(22):12132-37 (2000).

LeDouarin, Cell Line Segregation During Peripheral Nervous System Ontogeny, Science 231:1515-22 (1986).

Novikoff, et al., Stem Cells and Rat Liver Carcinogenesis: Contributions of Confocal and Electron Microscopy, Journal of Histochemistry & Cytochemistry 46: 613-26 (1998).

Sakurai, et al., Journal of Surgical Oncology 42:39-46 (1989).

Saati, et al., Blood, 74:2476-2485 (1989).

Makarovskiy, et al. "Comparative immunohistochemical analysis of normal and neoplastic prostate tissues using novel markers," *Proc of the American Association*. 39:201, Mar. 1998 abstract.

Halpert, et al. "Development of normal and SV40-large T immortalized dorsal-lateral rat prostate cell lines". *Proc of the American Association for Cancer Research Annual Meeting*, 37:508-509, 1996, abstract.

Uchida et al. "Direct Isolation of Human Neural Stem Cells From Fetal Brain By Cell Sorting", *Society for Neuroscience Abstracts*, 25 1-2:ABS70103, 1993, abstract.

(Continued)

*Primary Examiner*—Long V. Le
*Assistant Examiner*—James L. Grun
(74) *Attorney, Agent, or Firm*—Wilmer Cutler Pickering Hale and Dorr LLP

(57) ABSTRACT

The invention provides monoclonal antibodies that selectively bind to ectodermally- and endodermally-derived stem cells and methods for the diagnosis of a neoplasm in a subject by contacting a tissue sample from the subject with the antibodies. Also disclosed are methods for isolating such stem cells from a heterogeneous cell population by contacting the population with antibodies which selectively bind to stem cells.

18 Claims, 3 Drawing Sheets

OTHER PUBLICATIONS

Gu et al. "Monoclonal Antibodies Against Prostate Stem Cell Antigen (PSCA) Detect High Levels of PSCA Expression in Prostate Cancer Bone Metastates" *Journal of Urology*, 161 4,:126, 1999, *abstract*.

Ware et al., 1982. Production of monoclonal antibody αPro3 recognizing a human prostatic carcinoma antigen. Cancer Research 42: 1215-1222.

Stemple et al., 1992. Isolation of a stem cell for neurons and glia from the mammalian neural crest. Cell 71:973-985.

Zhau et al., 1992. Expression of c-*erb* B-2/*neu* proto-oncogene in human prostatic cancer tissues and cell lines. Molecular Carcinogenesis 5: 320-327.

Lo et al., 1995. Postmigratory neural crest cells expressing c-RET display restricted developmental and proliferative capacities. Neuron 15: 527-539.

Rokhlin et al., 1998. 5E10: a prostate-specific surface reactive monoclonal antibody. Cancer Letters 131: 129-136.

Bodey et al., 1996. Identification of neural crest derived cells within the cellular microenvironment of the human thymus employing a library of monoclonal antibodies raised against neuronal tissues. In Vivo 10: 39-48.

Trikha et al., 1996. Human prostate carcinoma cells express functional allbβ3 integrin. Cancer Research 56: 5071-5078.

Rao et al., 1997. Immortalization and controlled in vitro differentiation of murine multipotent neural crest stem cells. J. Neurobiology 32: 722-746.

* cited by examiner

COMPOSITIONS FOR IDENTIFICATION AND ISOLATION OF STEM CELLS

CROSS-REFERENCE TO RELATED APPLICATIONS

This application is a continuation of U.S. patent application Ser. No. 09/603,453 filed Jun. 22, 2000, entitled "Compositions for Identification and Isolation of Stem Cells," now U.S. Pat. No. 6,632,620.

FIELD OF THE INVENTION

The invention relates to stem cells.

BACKGROUND OF THE INVENTION

Stem cell populations have been identified in many tissues and are thought to constitute a source of tissue renewal in quiescent, regenerative and pathological conditions. Tumor stem cells are the cell renewal source of a neoplasm and also serve as the seeds of metastatic spread of cancer. While rapidly proliferating tissues such as bone marrow, gut, and epidermis are known to be organized into stem cells and lineages of maturing descendants, the evidence for parallel phenomena in other tissues has been debatable.

Stem cell markers are useful to diagnose cancers and to treat pathological conditions characterized by abnormal or insufficient function of differentiated cells of a mature organ. However, stem cells have been difficult to identify and isolate.

SUMMARY OF THE INVENTION

The invention features an antibody that selectively binds to an ectodermally-derived stem cell. Preferably, the antibody that selectively binds to an ectodermally-derived stem cell does not also bind to an endodermally-derived stem cell. More preferably, the antibody that selectively binds to an ectodermally-derived stem cell does not also bind to either an endodermally-derived stem cell or a mesodermally-derived stem cell. Such antibodies include MAb 13.2.7 or 1.33.2. For example, the antibody selectively binds to an epithelial stem cell, a skin stem cell, a neural stem cell, or an occular stem cell. Antibodies that selectively bind to an ectodermally-derived stem cell include MAb 7.22.3, 7.18.1, 7.18.9, 9.5.5, 9.29.1, 7.40.1, 6.39.2, 12.3.2, 6.9.2, 6.19.10, 13.2.7 or 1.33.2. The invention also includes an antibody which binds to an epitope identified by MAb 7.22.3, 7.18.1, 7.18.9, 9.5.5, 9.29.1, 7.40.1, 6.39.2, 12.3.2, 6.9.2, 6.19.10, 13.2.7 and 1.33.2. A method of isolating an ectodermally-derived stem cell from a heterogenous population of cells is carried out by contacting a heterogenous population of cells with one or more of the antibodies described above.

The invention also includes an antibody that selectively binds to an endodermally-derived stem cell. Preferably, the antibody does not bind to a bile duct stem cell or a liver stem cell. The antibody that selectively binds to an endodermally-derived stem cell does not bind to an ectodermally-derived stem cell and/or does not bind to a mesodermally-derived stem cell.

One example of an endodermally-derived stem cell-specific antibody is one that selectively binds to a prostate stem cell. In another example, the antibody selectively binds to a prostate stem cell and also selectively binds to a liver stem cell. Preferably, the antibody that selectively binds to a prostate stem cell and further selectively binds to a liver stem cell does not bind to a skin stem cell. For example, MAb 6.39.2 binds to a prostate and liver stem cell but not a skin stem cell.

The antibodies described herein are useful to identify and isolate tissue-specific stem cells. For example, a method of isolating an endodermally-derived stem cell from a heterogenous population of cells includes the step of the contacting population with an antibody that selectively binds to an endodermally-derived stem cell.

Yet another aspect of the invention is a method of diagnosing a neoplasm in a subject, by contacting a tissue sample from a subject such as a human patient with an antibody that selectively binds to an ectodermally-derived stem cells or one that selectively binds to an endodermally-derived stem cell.

Stem cells are also isolated by removing non-stem cells, i.e., differentiated or mature cells, from a heterogeneous population. Such a negative selection approach carried out alone or in combination with the positive selection method described above is useful to isolate stem cells. The invention encompasses an antibody selected from the group consisting of MAb 3.40.7, 5.37.1, 5.37.4, 8.36.1, 12.3.3, and 14.33.7. Such antibodies bind to cells which are not stem cells. A negative selection method of isolating a stem cell from a heterogenous population of cells involves contacting a heterogeneous population of cells with an antibody selected from the group consisting of MAb 3.40.7, 5.37.1, 5.37.4, 8.36.1, 12.3.3, and 14.33.7 under conditions to form an antibody-cell complex, and removing the complex from the population. Removal of non-stem cells (i.e., non-stem cell-Ab complexes) from the heterogeneous population of cells leaves a population of isolated stem cells. By a isolated population of isolated stem cells is meant a population of cells in which at least 70%, preferably 80%, preferably 85%, preferably 90%, more preferably 95%, more preferably 99% of the cells are stem cells. For example, the population is 100% stem cells. The percentage of stem cells in a population of cells is determined by known methods such as fluorescence-activated cell sorting.

The invention encompasses not only an intact monoclonal antibody, but also an immunologically-active antibody fragment, e.g., a Fab or $(Fab)_2$ fragment; an engineered $F_v$, molecule; or a chimeric molecule, e.g., an antibody which contains the binding specificity of one antibody, e.g., of murine origin, and the remaining portions of another antibody, e.g., of human origin. Preferably, the antibody has a binding affinity of at least about $10^8$ liters/mole and more preferably at least about $10^9$ liters/mole. Humanized monoclonal antibodies are also within the invention. Monoclonal antibodies of non-human origin, e.g., mouse monoclonal antibodies, are humanized by methods known in the art. For example, mouse monoclonal antibodies with a desired binding specificity are commercially humanized (Scotgene, Scotland or Oxford Molecular, Palo Alto, Calif.).

By "selectively binds" is meant that the antibody binds to stem cells with at least 50% greater affinity than the affinity with which it binds to a known differentiated or mature cell, preferably at least 60%, preferably at least 70%, preferably at least 80%, preferably at least 85%, preferably at least 90%, more preferably at least 95%, more preferably at least 99% greater. The binding affinity of an antibody can be determined by methods known in the art.

All technical and scientific terms used herein have the same meanings commonly understood by one of ordinary skill in the art to which this invention belongs. Although any methods and materials similar or equivalent to those described herein can be used in the practice of the present invention, the preferred methods and materials are now described. The citation or identification of any reference within this application shall not be construed as an admission that such reference is available as prior art to the present invention. All publications mentioned herein are incorporated herein in their entirety by reference.

DETAILED DESCRIPTION OF THE INVENTION

Figure 1:
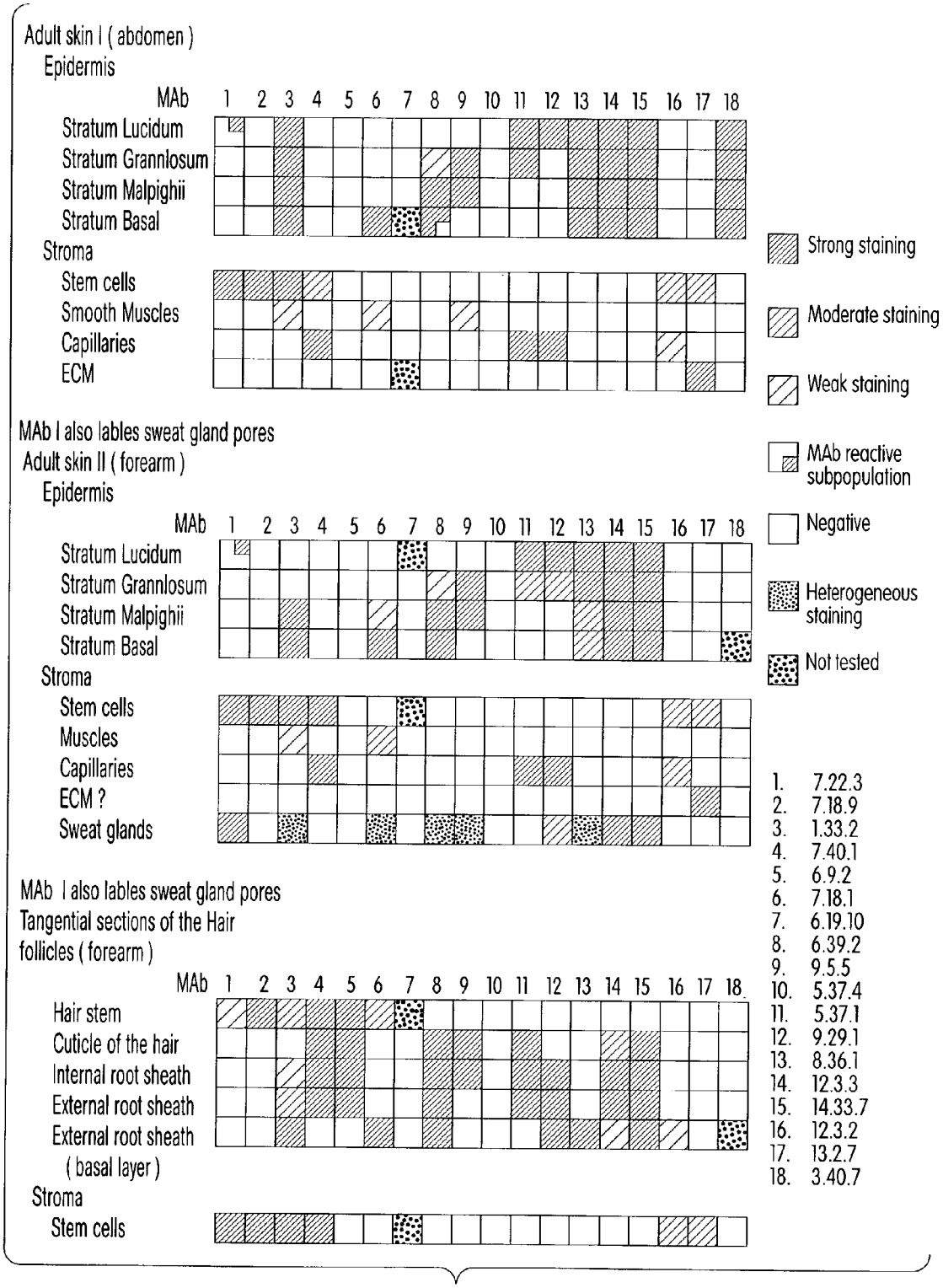
FIG. 1 is a diagram showing tissue binding patterns of monoclonal antibodies 7.22.3; 7.18.9; 1.33.2; 7.40.1; 6.9.2; 7.18.1; 6.19.10; 6.39.2; 9.5.5; 5.37.4; 5.37.1; 9.29.1; 8.36.1; 12.3.3; 14.33.7; 12.3.2; 13.2.7; and 3.40.7.

Stem cells are identified by one or more of the following properties: a) relatively undifferentiated, b) capable of maintaining their small numbers through asymmetric cell divisions producing at least one stem cell, c) possessing essentially unlimited proliferative potential, d) pluripotent or capable of giving rise to all cell types of a particular tissue, e) capable of tissue regeneration, and f) being able to adapt to changes in their environment. Pluripotentiality or the ability to differentiate into the full range of daughter cells having distinctly different morphological, cytological or functional phenotypes unique to a specific tissue was named a key stem cell property. By contrast, descendants of stem cells are restricted progressively in their differentiation potential, with some cells having only one fate. Three broad lineage classes of cells have been defined: a) stem cells, b) amplifying cells, and c) postmitotic cells. As used herein, stem cells are defined as cells having the ability to proliferate indefinitely. Progenitor cells, on the other hand, are cells that do not have the ability to proliferate indefinitely. Progenitor cells are typically limited to 60–70 doublings, as predicted by Hayflick's limit.

Table 1 shows some examples of ectodermally,-mesodermally,- and endodermally-derived tissues. As used herein, the terms ectodermal, mesodermal, and endodermal are understood to encompass these tissues along with other tissues known to one skilled in the art to be derived from the ectoderm, mesoderm, and endoderm.

For the production of monoclonal or polyclonal antibodies, various suitable host animals (e.g., rabbit, goat, mouse or other mammal) are immunized by injection with cells (e.g., tumor xenograft cells such as those shown in FIG. 3) or a protein (e.g., a purified naturally-occurring protein or a synthetic variant thereof). For example, the immunogen is a protein that is preferentially expressed on a stem cell compared to a mature or differentiated cell. An appropriate immunogenic preparation can contain, for example, recombinantly expressed antigen/epitope or a chemically synthesized antigen/epitope polypeptide. The preparation may also include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as *Bacille Calmette-Guerin* and *Corynebacterium parvum*, or similar immunostimulatory agents. If desired, the antibody molecules directed against ectodermally- or endodermally-derived stem cells can be isolated from the mammal (e.g., from the blood) and further purified by well known techniques, such as protein A chromatography to obtain the IgG fraction.

The term "monoclonal antibody" or "monoclonal antibody composition", as used herein, refers to a population of antibody molecules that contain only one species of an antigen binding site capable of immunoreacting with a particular epitope of an ectodermally- or endodermally-derived stem cell. A monoclonal antibody composition thus typically displays a single binding affinity for a particular antigen/epitope with which it immunoreacts. For preparation of monoclonal antibodies directed towards a particular antigen/epitope, or derivatives, fragments, analogs or homologs thereof, any technique that provides for the production of antibody molecules by continuous cell line culture may be utilized. Such techniques include, but are not limited to, the hybridoma technique (see Kohler & Milstein, 1975 *Nature* 256: 495–497); the trioma technique; the human B-cell hybridoma technique (see Kozbor, et al., 1983 *Immunol Today* 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77–96). Human monoclonal antibodies may be utilized in the practice of the present invention and may be produced by using human hybridomas (see Cote, et al., 1983. *Proc Natl. Acad Sci USA* 80: 2026–2030) or by transforming human B-cells with Epstein Barr Virus in vitro (see Cole, et al., 1985 In: MONOCLONAL ANTIBODIES AND CANCER

TABLE 1

| Tissue Derivation Examples | | |
|---|---|---|
| Ectoderm | Mesoderm | Endoderm |
| Skin & Specialized Structures (hair, nails, etc.) | Musculoskeletal System | Digestive System |
| Nervous System | Circulatory System | Parts of the Respiratory System |
| Organs of special sense (ear & eye) | Connective Tissue | Lining of the Alimentary Tract and Lungs |
| Exocrine glands (sweat & sebacious glands) | Excretory System/Kidneys | |
| Endocrine glands (pineal body and pituitary gland) | Reproductive System/Gonads | |
| | Blood | |

THERAPY, Alan R. Liss, Inc., pp. 77–96). Each of the above citations are incorporated herein by reference in their entirety.

According to the invention, techniques can be adapted for the production of single-chain antibodies specific to a endodermally- or ectodermally-derived stem cell (see e.g., U.S. Pat. No. 4,946,778). In addition, methods can be adapted for the construction of $F_{ab}$ expression libraries (see e.g., Huse, et al., 1989 Science 246: 1275–1281) to allow rapid and effective identification of monoclonal $F_{ab}$ fragments with the desired specificity. Non-human antibodies can be "humanized" by techniques well known in the art. See e.g., U.S. Pat. No. 5,225,539. Each of the above citations are incorporated herein by reference. Antibody fragments that contain the idiotypes to a particular antigen/epitope may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $Fl_{(ab')2}$ fragment; (iii) an $F_{ab}$ fragment generated by the treatment of the antibody molecule with papain and a reducing agent and (iv) $F_v$ fragments.

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al. (1988) Science 240:1041–1043; Liu et al. (1987) PNAS 84:3439–3443; Liu et al. (1987) J Immunol. 139:3521–3526; Sun et al. (1987) PNAS 84:214–218; Nishimura et al. (1987) Cancer Res 47:999–1005; Wood et al. (1985) Nature 314:446–449; Shaw et al. (1988), J. Natl Cancer Inst 80:1553–1559); Morrison (1985) Science 229: 1202–1207; Oi et al. (1986) BioTechniques 4:214; U.S. Pat. No. 5,225,539; Jones et al. (1986) Nature 321:552–525; Verhoeyan et al. (1988) Science 239:1534; and Beidler et al. (1988) J Immunol 141:4053–4060. Each of the above citations is incorporated herein by reference.

In one embodiment, methods for the screening of antibodies that possess the desired specificity include, but are not limited to, enzyme-linked immunosorbent assay (ELISA) and other immunologically-mediated techniques known within the art. In a specific embodiment, selection of antibodies that bind selectively to an ectodermally- or endodermally-derived stem cell is facilitated by generation of hybridomas, which produce an antibody that binds to the stem cell with a greater affinity than the affinity with which it binds to a differentiated cell.

Antibodies may be used in methods known within the art relating to the localization and/or quantitation of stem cells (e.g., for use in measuring levels of the stem cells within appropriate physiological samples, for use in diagnostic methods, for use in imaging the stem cells, and the like). Antibodies for specific stem cells are utilized as pharmacologically-active compounds.

An anti-stem cell antibody (e.g., monoclonal antibody) is used to isolate stem cells by standard techniques, such as affinity chromatography or immunoprecipitation. Moreover, an anti-stem cell antibody is used to detect stem cells or tumor cells which pathologically express the stem cell antigen (e.g., in a tissue sample, a cellular lysate, or a cell supernatant) in order to evaluate the abundance and pattern of expression of the stem cells or tumor cells. Anti-stem cell antibodies are used diagnostically to monitor tumor levels in tissue as part of a clinical testing procedure, e.g., to, for example, determine the efficacy of a given treatment regimen. Detection is facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include 125I, $^{131}$I, $^{35}$S or 3H.

Generation of Monoclonal Antibodies

Figure 3:
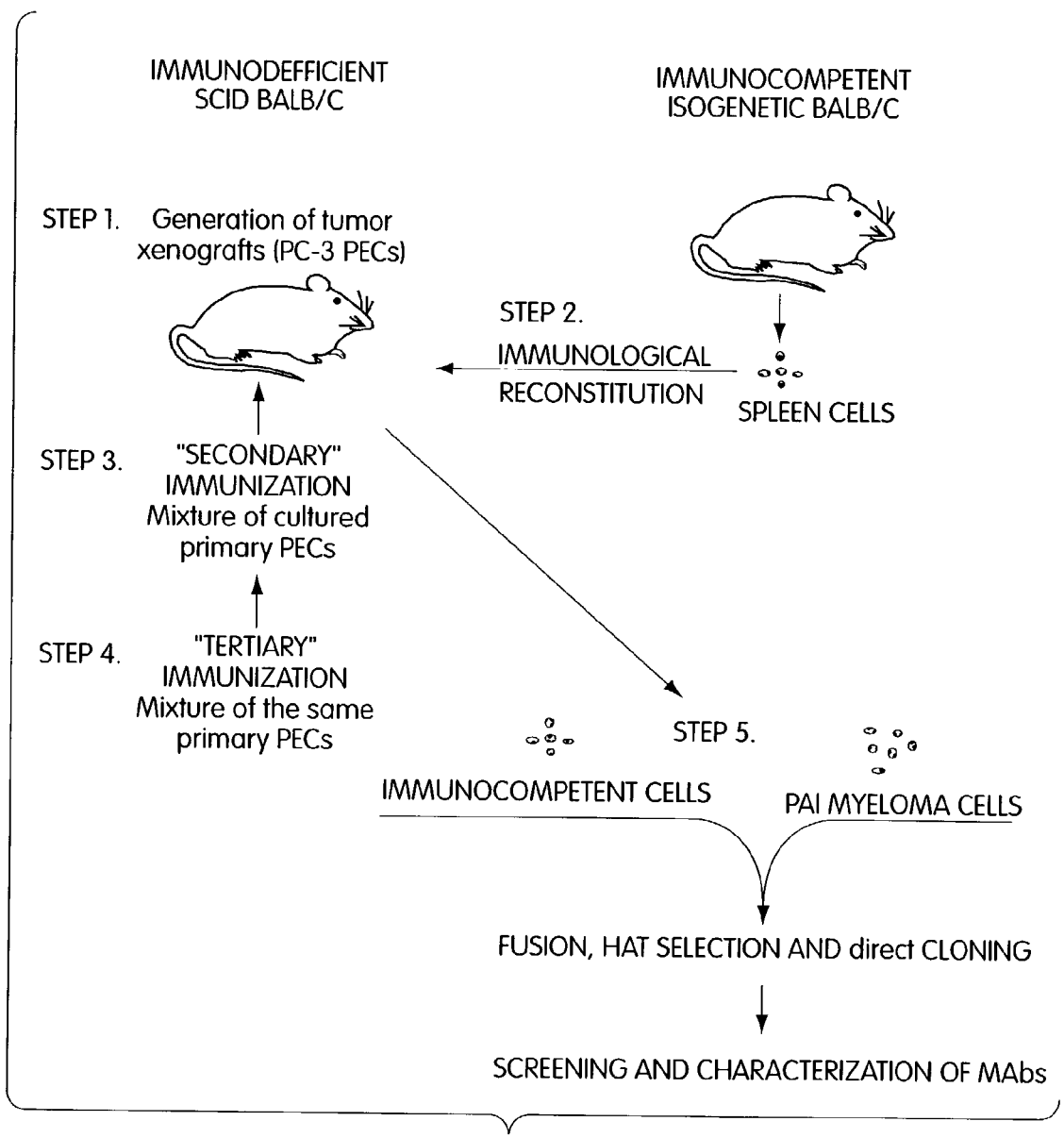
FIG. 3 is a diagram of an immunization strategy for production of MAb which selectively bind to stem cell antigens.

Monoclonal antibodies which bind to developmental surface antigens are useful for detecting, isolating and studying the marker defined cell populations. Useful MAbs that detect various surface antigens are produced by immunizing mice with live cells. The immunization strategy shown in FIG. 3 is used to identify new surface specific markers on ectodermally- and endodermally-derived stem cells.

A method used to generate stem cell specific monoclonal antibodies follows. First, human or other mammalian donor cells were grafted into an immunodeficient host animal. These donor cells can be normal or tumor cells. Preferably, these cells are metastatic tumor cells (target cells) or various mixtures of normal, tumorous, and metastatic tumorous cells. The animal host is preferably a Severely Combined Immunodeficient ("SCID") mouse. The graft generated by the target cells is generated by prefereably subcutaneous, intravenous or intraperitoneal and less preferably, intradermal injection of cells. The donor cells were allowed to expand, establish colonies in the new micro environment, and express representative complement of donor cell surface, cytoplasmic, and nuclear antigens/epitopes. Preferably, donor cell engraftment is for not less than one day and preferably less than 60 days.

Second, a primary immune response to the grafted cells was induced in the graft-bearing immunodeficient host. This was accomplished by transplanting naive, immunocompetent cells derived from a genetically identical immunocompetent donor animal. These transplanted immunocompetent donor cells were used to reconstitute the immune system of the immunodeficient host animal and generate lymphocytes that produce antibodies to surface, nuclear, and cytoplasmic antigens presented by grafted human or animal cells but not to the cells of the gentically identical graft-bearing immunodeficient host.

Third, the primary immune response was amplified. This step is necessary to increase the immune response against antigens present in grafted cells and/or cells of the same or different human or animal tissue. The amplification was accomplished by secondary and higher order immunizations. Such immunizations are typically performed by intraperitoneal injection, less preferably intravenous and least preferable intradermal or subcutaneous injection of the cells used to generate the initial graft. Immunizations could include primary normal and/or tumor cells or mixtures of such cells derived from the same or different human tissue as the origin of the grafted cells. Live cells derived from human or other animal tissues and used for the secondary immunizations are either freshly isolated or cultured for a short or long period of time, preferably in a media supporting survival and expansion of the stem cells in culture. Alternatively, continuous tumor or normal cell lines close in origin to the grafted cells are used for the purpose of secondary and/or higher order immunization. At least two such immunizations should be carried out to induce strong immune response and facilitate generation and expansion of the immunocompetent cells secreting antibodies that recognize a wide spectrum of antigens. Such immunizations were carried out at least 1 day (e.g., 7–10 days) after the immunological reconstitution of the graft-bearing animal host and repeated at least twice.

Fourth, cell lines secreting monoclonal antibodies were produced. This was accomplished by immortalizing the graft bearing animal host lymphocytes derived from spleen and peripheral lymph nodes. The immortal cell lines produced according to this immunization protocol were separated from one another immediately or soon after the immortalization step. This separation is accomplished by cloning in methylcelulose or agar or other semisolid gel like media containing nutrients supporting expansion of the antibody producing cells. Alternatively, the well-established approach of cloning antibody producing cells by limiting dilution is used. Immediate isolation and cloning facilitates the non-competitive growth of the cell lines and enables the isolation of both fast and slow growing cell lines secreting antibodies.

Finally, the fifth step of this immunization strategy involved the screening of the monoclonal antibodies produced by the immortalized animal lymphocytes for the specific and desired stem cell-specific reactivity. Screening was performed to identify those immortalized cell lines secreting antibodies against epitopes expressed by the stem cell and/or their progeny of a desired target tissue. This type of screening will enable identification of rare antigens specifically expressed in all or subpopulation of cells comprising the tissue (including the heterogeneous population of stem cells of the particular tissue). The produced MAbs are screened for their specific reactivity by a method, or a combination of methods, such as immunohistochemistry or the combination of immunohistochemistry and immunocytochemistry to determine the pattern of distribution of the antibody-reactive antigens in the tissue. In this way, clones reactive with few cells or larger subpopulations or all of the cells comprising the tissue are identified.

To identify the immortalized cell lines secreting antibodies produced in the target tissues and released into body fluids such as urine, blood serum, or plasma, the MAbs were screened for their specific reactivity by an immunologic assay such as ELISA, Western Blot, or other similar techniques that allow the determination of positive or negative antibody reactivity. This approach is used to identify antibody clones capable of detecting appearances, disappearances, or changes in the concentration of the antibody-reactive antigens in body fluids in a certain disease or condition by comparison with samples of fluids collected from normal controls.

Deposit

A deposit of the hybridoma cell line, which produces mAb 7.22.3 disclosed above and recited in the appended claims, has been made with the American Type Culture Collection (ATCC), 10801 University Boulevard, Manassas, Va. 20110 under the terms of the Budapest Treaty on the International Recognition of the Deposit of Microorganisms for the Purpose of Patent Procedure on Sep. 10, 2002 and bears the ATCC accession number PTA-4655. All restrictions upon the deposit have been removed, and the deposit is intended to meet all of the requirements of 37 C.F.R. §§ 1.801–1.809. The deposit will be maintained in the depository for a period of 30 years, or 5 years after the last request, or for the effective life of the patent, whichever is longer, and will be replaced if it becomes non-viable during that period.

Uses of Stem Cell-Specific Monoclonal Antibodies

Monoclonal antibodies according to the invention have numerous uses and applications, including, e.g., diagnosis, selection and isolation of ectodermally- and endodermally-derived stem cells, and/or therapeutic assays. Monoclonal antibodies that specifically bind to stem cells or their descendants are also useful research tools to identify an assay for a wide variety of human growth factors and to further enable the characterization of stem cells. Monoclonal antibodies against stem cells could serve as a useful research tool to study normal human or other mammalian development, to identify cellular events leading up to various diseases and affecting stem cell during development or in adult mammals. These antibodies could also be used as reference markers to develop other new antibodies against stem cells and their descendants.

Diagnostic Assays

The monoclonal antibodies described herein serve as markers of tumor stem cells and their progeny. Thus, they are useful for the detection of various cancers, the monitoring of cancerous progression, and/or the prediction of the disease course. Monoclonal antibodies are used to develop methods for detecting carcinomas and their cellular progenitors as well as tumor stem cells. The diagnostic assays described herein are performed, e.g., by utilizing pre-packaged diagnostic kits comprising at least one antibody reagent described herein. Such kits are used in clinical settings to diagnose patients exhibiting warning signs, symptoms, or family history of a disease, of cancer, or of an illness involving a stem cell pathology (e.g., an abnormally high or low level of a particular stem cell).

Diagnostic assays are used for determining the presence or number of ectodermally- and/or endodermally-derived stem cells in the context of a biological sample (e.g., blood, serum, cells, tissue) to determine whether an individual is afflicted with a disease or disorder, or is at risk of developing a disorder, associated with aberrant ectodermally- or endodermally-derived stem cell levels. The invention also provides for prognostic (or predictive) assays for determining whether an individual is at risk of developing a disorder associated with ectodermally- or endodermally-derived stem cell levels. For example, aberrant levels of ectodermally- or endodermally-derived stem cells is assayed in a biological sample. Such assays are used for prognostic or predictive purpose to thereby prophylactically treat an individual prior to the onset of a disorder characterized by or associated with ectodermally- or endodermallyderived stem cell expression. For example, a pathological condition characterized by an abnormally low level of stem cells is treated by administering to the individual a population of isolated stem cells. These cells can be administered intraveneously at $10^5$–$10^9$ cells per treatment, e.g. $10^9$ cells intravenously infused over 30 minutes. Conversely, a condition characterized by an abnormally high level of stem cells or a cancer characterized by expression of a stem cell marker is treated by ablating cells expressing the marker. Undesired cells are ablated by contacting the cells with the stem cell-specific antibodies described herein. The antibodies are tagged with a cytotoxic agent to kill undesired cells. Alternatively, the cells are contacted with an antibody followed by contacting the cell-antibody complex with a cytotoxic agent.

Diagnostic assays according to the instant invention may-include for example; a method of diagnosing a neoplasm in a subject. In one embodiment, this diagnostic method involves the following steps: a) providing a test cell population from the subject; b) contacting the test cell population with an antibody that selectively binds to ectodermally- or endodermally-derived stem cells; c) measuring the level of antibody binding of the antibody to the test cell population; d) comparing the level of antibody binding to the cell sample with the extent of binding in a reference cell population whose neoplastic state is known; and e) identifying a difference in the extent of antibody binding, if present, in the test cell population and reference cell population. In this way, a neoplasm may be diagnosed, if present in the subject.

A method for diagnosing a tumor is carried out by contacting a patient-derived tissue sample with a stem cell-specific antibody and measuring the level of binding. The level of binding is compared to a predetermined standard control value or the level of binding in a tissue sample known to be noncancerous. A higher level of binding in the patient-derived tissue sample compared to the control or known normal tissue indicates the presence of a tumor cell in the patient-derived sample.

Selection and Isolation of Endodermally- and Ectodermally-Derived Stem Cells

The monoclonal antibodies according to the instant invention recognize stage-specific antigens on immature human cells. Thus, these monoclonal antibodies are useful in methods to detect and isolate cell suspensions comprising cellular compositions of ectodermally and endodermally derived immature mammalian cells or stem cells present in human organ. Immature normal human cells are characterized by the expression of cytokeratins or the lack of essential expression of cytoderatins or other currently known mature tissue-specific markers. Often, they are fixed in position within the stromal mesenchymal cells by their own basement membranes. These immature cells maintain their small numbers through an asymmetric cell cycle in vivo and in vitro. They are small in size and possess a low nuclear to cytoplasm ratio. Additionally, they play a central role in maintaining tissue homeostasis, and, at least a portion of these immature cells is capable of differentiating into more mature cells expressing cytokeratins or other mature tissue-specific markers.

Monoclonal antibodies are used to isolate highly concentrated compositions of stem cells that are substantially free of differentiated or dedicated cells. Additionally, the provided monoclonal antibodies enable the isolation of certain fractions of stem cells. For example, the monoclonal antibodies of the invention are used to isolate a substantially pure population of stem cells from a heterogeneous cell population or cell sample. The monoclonal antibodies are also used to isolate a particular stem cell fraction, e.g. a tissue specific are stage specific stem cell, from a heterogeneous stem cell population or stem cell sample.

According to these methods, the cells are obtained by positive selection of the desired cell populations defined by a single monoclonal antibody or by a combination of antibodies. Alternatively, the cells are obtained by negative selection of undesired cell populations using a single monoclonal antibody or a combination of antibodies. The resulting composition(s) are cultured and expanded with or without differentiation. Such normal cellular compositions are used to reconsitute the stem cells of the host. The compositions can also be transfected with foreign nucleic acid molecules to produce an immortalized epithelial stem cell or a stem cell genetically engineered to express proteins or polypeptides of interest. Additionally, the provided monoclonal antibodies are useful to identify, isolate, and/or therapeutically target human tumor stem cells and their descendants.

In contrast to the methods described herein, the methods of isolating progenitor cells described in the prior art note that progenitor cells could be isolated by binding monoclonal antibodies raised against known growth factor receptors (such as EGF or FGF, etc.) to the progenitor cells expressing these receptors. This cell population is then isolated from the cells not expressing these growth factor receptors by FACS sort, immunobeads, or panning techniques.

Expression of the growth factor receptors by the progenitor cells was determined by exposing micro-organoid cultures to mitogenic factors, e.g. receptor ligands. The methods described herein yield a more highly purified population of stem cells because the growth factor receptors described in earlier methods are shared with more mature cells and/or stem cell progeny. Thus, the process of purifying stem cells using the methods described in the prior art are compromised and the resulting cell suspensions will always contain "non-stem cells"

The earlier approach to use monoclonal antibodies to known growth factor receptors that are expressed by stem cells and their progeny precludes clear detection of the stem cells. For example, tissue labeling experiments using known receptor-specific antibodies results in detection of both stem cells and their progeny. To circumvent this problem, the methods of the prior art involve a two-step process that involves culturing tissue organoids in the presence of mitogens stimulating preferential expansion of the stem cells followed by further purification by mechanical or chemical means. Determination of the stem cell expansion in the resulting cultures is based on the morphologic criteria of the resulting organoids comprised of the stem cells along with non-stem cells. The assessment of stem cell expansion of earlier methods is always indirect and enumeration of the stem cells is not possible.

One variation of the invention includes a negative selection step. Earlier methods do not include a "negative selection" method of enriching a desired cell population of the instant invention. Negative selection is based on the removal of the mature cells or stem cell progeny either mechanically, biochemically, or using the antibodies according to the invention to collect the cells that are negative for mature cell markers (e.g. stem cells). This technique enhances the isolation of enriched stem cell populations.

Current regulations on the therapeutic use of cells in clinical practice do not allow introduction of animal proteins (including mouse monoclonal antibodies) into a human patient. This would preclude the use of stem cells coated with mouse antibodies. In addition, it would require detachment of the antibody from the stem cell. The negative selection method allows removal of non-stem cells. By analyzing the resulting cell fraction for the presence of stem cells using cell-type specific markers, the purity of the fraction is augmented. This can be accomplished by the "negative selection" approach using antibodies such as MAb 3.40.7, 5.37.1, 5.37.4, 8.36.1, 12.3.3, and 14.33.7.

Therapeutic Uses

The monoclonal antibodies according to the invention are useful to treat carcinomas. Populations of the stem cells defined by these monoclonal antibodies and involved in neoplasia and/or benign disease are a likely primary target for the development of novel therapies. Such therapies are based on the elimination and/or repair of the impaired stem cells associated with the neoplasia or benign disease.

Additionally, populations of normal adult, fetal or embryonic stem cells defined by the monoclonal antibodies of the instant invention can be isolated, optionally expanded, and used as a basis for the cellular therapy. For example, such stem cells can serve as a primary cellular material to generate desired new tissue such as liver, pancreas, skin, or other tissue to be used as a replacement organ or part of the organ or as a cellular material for extracorpora tissue replacement.

The invention provides for both prophylactic and therapeutic methods of treating a subject at risk of (or susceptible to) a disorder or having a disorder associated with aberrant ectodermally- or endodermally-derived stem cell expression or aberrant proliferation of cells expressing a stem cell marker.

Characterization of Monoclonal Antibodies

According to the methods described herein, a panel of monoclonal antibodies was generated. Monoclonal antibodies were found to be reactive with surface antigens/epitopes that are expressed selectively in stem cells or progenitor cells. These antibodies include, for example, clones 7.22.3; 7.18.1; 7.18.9; 9.5.5; 9.29.1; 7.40.1, 6.39.2; 12.3.2; 6.9.2, 6.19.10, 13.2.7, and 1.33.2, or antibodies having similar antigen binding specificities to any of these. Clones 1.33.2 and 13.2.7 enable one skilled in the art to distinguish between ectodermally- and endodermally-derived stem cells. In other words, endodermally-derived stem cells lack expression of these markers.

Other antibodies in the panel provide means to identify, characterize or isolate heterogeneous cellular populations of the stem cell progeny or descendants developing along multiple lineages. In addition, the invention includes monoclonal antibodies that label surface epitopes on mature cells. These include MAb 3.40.7, 5.37.1, 5.37.4, 8.36.1, 12.3.3, and 14.33.7.

Figure 2:
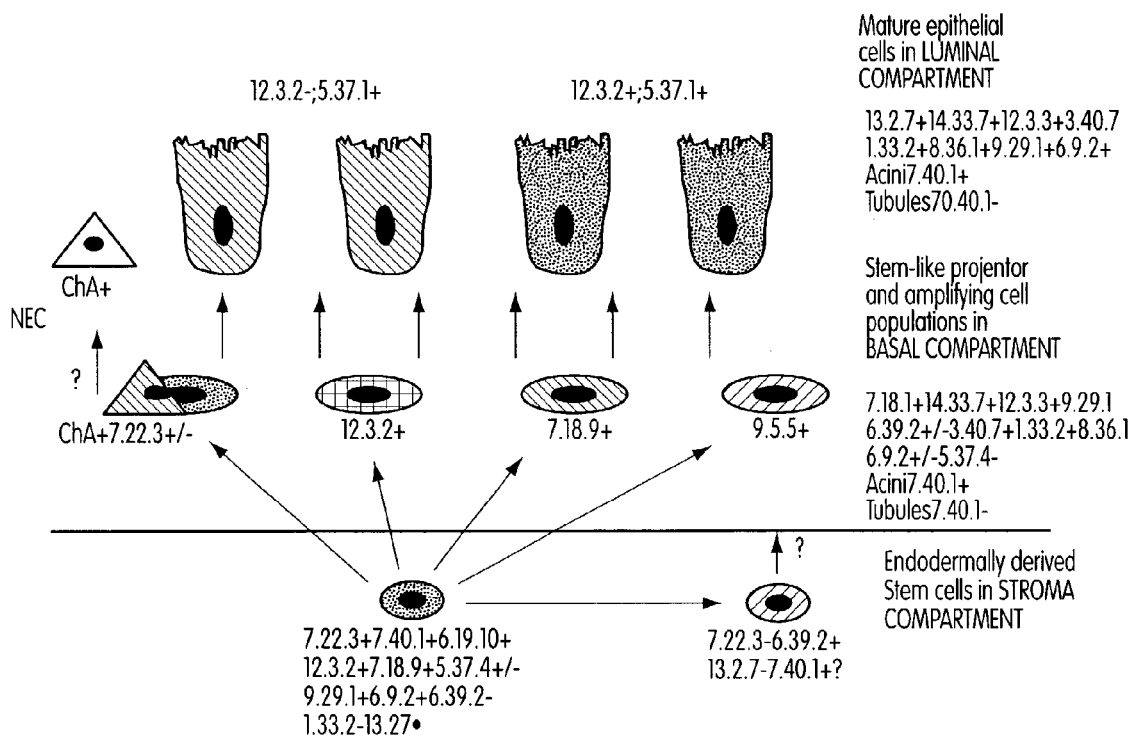
FIG. 2 is a diagram showing the cell type-specific distribution of surface epitopes detected with a panel of MAb in adult normal human prostate.

An example of the characterization of the monoclonal antibodies is demonstrated in FIGS. 1 and 2. FIG. 1 is a diagram of MAb which selectively bind to prostate stem cells. FIG. 2 is a diagram of MAb which selectively bind to skin stem cells.

EXAMPLES

The invention will be further described in the following examples, which do not limit the 20 scope of the invention described in the claims.

Example 1

Generation of MAbs Against Human Prostate Cells

Severely Combined Immunodeficient (SCID) Balb/c mice bearing 4–6 mm in diameter subcutaneous colonies of the prostate cancer cell line PC-3, were injected intraperitoneally with spleen cells derived from normal syngeneic mice (Balb/c) to perform host immunological reconstitution and primary immune response. To amplify the immune response against epitopes common to different isolates of prostate cancer cells, two weeks later a round of booster immunization was performed be injecting intraperitoneally mixtures of two low passage primary prostate carcinoma strains. Three secondary immunizations were performed using the same mixture of cells. Immunizations were performed at a 7 to 10 day interval.

The quality of immunological reconstitution and immune response was assessed in a direct ELISA of mouse serum to detect a progressive increase in total immunoglobulin (Ig) titer. Three days after the last immunization, the Ig titers became sufficient and immune cells from spleen and peripheral lymph nodes were harvested and fused with PAI mouse myeloma cells to produce hybridomas. 24 hours after the fusion, the hybridoma cells were suspended in a methylcellulose containing media (StemCell Technologies) to facilitate HAT selection and separation of individual hybridoma clones. Once sufficiently grown, clones were isolated and expanded in 96 well dishes in standard Iscove's media. An aliquot of spent media was collected and tested for specific MAb reactivity with frozen sections prepared from PC-3 tumor nodules and tissue samples from normal and primary prostate cancer specimens.

Thirty seven clones that showed patterns of reactivity suggestive of the surface antigen/epitope localization were selected, expanded, and recloned by limiting dilution or in methylcellulose containing media to ensure monoclonality of antibodies. Supernatants rich in MAb hybridomas were collected and used throughout the described studies at appropriate dilutions. The isotype of each of the 37 selected MAb was determined using MAb isotyping kit from Zymed. The selected (and most of the unscreened hybridoma clones) were cryopreserved in liquid nitrogen to provide resources for future studies.

Example 2

Characterization of the Selected Monoclonal Antibodies

The results of the initial MAb screening for reactivity with frozen sections prepared from normal or tumor tissues suggested selected MAb are strongly reactive with prostatic epithelial cells producing homogeneous or heterogeneous patterns of staining. To confirm consistency of identified patterns single labeling IIF analysis of tissue specimens used in initial screening were repeated using both polyclonal or mouse MAb isotype-specific secondary antibodies conjugated to FITC or Texas Red flourochromes. Two additional normal prostate tissues and six primary prostatic carcinoma specimens were also tested to augment the analyses and to collect initial data exemplifying consistent or changing patterns of antigen expression in normal or malignant prostate.

Using a topographic scheme based on the spatial relationship of the MAb-reactive prostatic cells, consistently reactive cell types in normal adult prostate were organized to facilitate systematic analysis. This topographic scheme was constructed to organize the staining patterns displayed by the different MAb in the context of prostate histological organization. MAb reactive cells in normal prostate were subdivided into four types: 1) Luminal cells (LC)—in direct contact with the glandular lumen; 2) Intermediate cells (IC)—located above the basal and underneath the luminal cells; 3) Basal cells (BC)—directly adjacent to the basal membrane, separating them from the stromal compartment but with no direct contact with the lumen; and 4) Single cells in stroma ("SCS")—a very small population of MAb reactive cells located in stroma with the majority in close proximity to the basement membrane. Several MAb clones were reactive with this unknown and rare cell type. Some MAb shared reactivity with either basal or basal and luminal prostatic cells and this new cell type. Negative reactivity with anti-Factor VIII antibodies excluded the possibility SCS were endothelial cells. Stromal localization of SCS was confirmed by double labeling IIF and confocal microscopy using MAb SCS7 in combination with polyclonal antibodies against heparan sulfate and/or collagen Type IV, two of the major constituents of the basement membrane.

When the SCS were present as doublets, each cell in the pair was surrounded not only by its own basement membrane but also a second layer surrounding both cells. This finding indicated that Factor VIII negative SCS in prostate are epithelial in nature and occupy a dedicated and distinct anatomical compartment. Double staining IIF with MAb SCS7 (FITC) and propidium iodide (PI) (nuclei) showed a low nuclear to cytoplasm ratio in SCS which ranged from 10 to 12 um in diameter. The PI-labeled chromatin was also tightly packed suggesting the cells were not mitotically active, a finding made in three separate experiments. The latter observation is confirmed by in situ labeling with BrDU. Compiled data was systematized as scheme to consider major and minor cell types populations organized along the axis perpendicular to the basement membrane. It reflects the small size MAb-reactive populations along the horizontal axis and subdivides prostatic ducts into acini and tubules using MAb SA7. Hierarchical relationships were proposed based on the IIF labeling data both in tissue and in vitro and initial results of SCS7+ cell fractionation.

A number of MAb in normal and carcinoma tissue specimens labeling experiments showed specificity to cell populations of various size and reacted with one or more specific cell types. To classify MAb clones specific to the same or different cell types, several double and triple labeling IIF protocols were optimized to allow simultaneous use of at least two new MAb with frozen tissue specimens or cultured cells. Labeling by combining two isotype-mismatched MAb and a polyclonal antibody (PAb) produced in another host (rabbit, rat or hamster) was used in some studies to simultaneously visualize three different antigens. This technique is especially helpful to discriminate the specificity of the new MAb to certain cell types by using an established cell type specific immuno markers as a reference. Neuroendocrine cells were localized with polyclonal antibody to Chromogranin A (ChA) from Dako. Only few ChA+/SCS7+ cells in stroma were identified in five consecutive sections while total number of SCS was close to a hundred. In contrast, expression of ChA in SCS7+ cells in carcinomas was more frequent. Antigens consistently coexpressed within a given cell type or types in normal prostate were considered cell type specific if random intermediate phenotypes disregarded. Identification of cells coexpressing cell type antigens in normal adult prostate tissue to indicate intermediate phenotype was an infrequent finding in the analysis of SCS vs. basal, intermediate or luminal cell types. Due to the slow turnover of mature cells, low numbers of cells in intermediate stages of differentiation resulted. Nevertheless, a number of antigenic links between minor and major subpopulations of cells in the context of tissue architecture has been established by this analysis.

Based on performed analyses a panel of nine out of 37 MAb showing stable patterns of cell type specific reactivity was selected for the current application. A pair of MAbs different in isotype but specific to the same cell type was chosen to facilitate crossreference in cell types detection and isolation in proposed studies. One MAb labeled nuclear epitope in most of prostate epithelial cells ("PEC") with an exception of SCS7+ cells, which, in contrast, demonstrated lack of nuclear localization. However, these cells did show surface localization of this epitope.

Several alterations of antigen expression in tested primary carcinoma specimens were identified. Expression of MAb 7.18.1 and 6.39.2 epitopes was redistributed from basal cells to luminal in some carcinoma foci or retained by tumor cells in basal position in others, or shifted from basal cells to SCS. MAb clone SCS7, which only labeled SCS in normal prostate showed heterogeneous antigen expression by foci of neoplastic prostate epithelial cells in different tumors. Interestingly, only small regions within the tumors were labeled by these MAbs. These areas were frequently void of SCS and were represented by small glandular-like structures of poorly differentiated cells. Contrary to expression in normal prostate, the epitope recognized by MAb SCS7 was also detected at times on small capillaries and venules as determined by double labeling IIF with anti-Factor VIII polyclonal antibody (Chemicon).

Example 3

Patterns of New MAb Reactivity in Vitro

To select the MAb clones potentially useful to fractionate MAb reactive viable cell populations reactivity was assayed by IIF labeling PC-3, DU-145, LNCaP continuous prostatic carcinoma cell lines obtained from ATCC collection. Cells were cultured in plastic dishes under standard conditions or grown to preconfluency in permanox coated chamber slides for phenotype analysis. This series of experiments disclosed a high degree of phenotypic heterogeneity and a marked differential in surface antigen expression within and between each cell line (Table 2).

TABLE 2

Reactivity with CaP lines

| Mab clone # | Cell line designation | | | |
|---|---|---|---|---|
| | PC-3 | DU-145 | LNCaP | ARCaP |
| MAb against SCS | | | | |
| SCS7 | 1–3% | Negative | Negative | Negative |
| MAb against SCS Shared with Subsets of BC | | | | |
| SB6 | 50–60% | Negative | Negative | 5% |
| 7.18.9 | <1% | Negative | 100% | 50% |
| MAb against SCS and glandular BC and LC | | | | |
| SA7 | 100% | 50% | 50% | 75% |
| MAb against subsets of Basal PEC | | | | |
| 9.5.5 | 5% | <1% | 100% | 50% |
| MAb against most of Basal PEC | | | | |
| 2.25.3 | 100% | 10–20% | Negative | Negative |
| 7.18.1 | 30% | 100% | Negative | 100% |
| MAb against most of the Luminal PEC | | | | |
| 13.2.7 | 50% | Negative | Negative | 75% |
| MAb against most of the Basal and Luminal PEC | | | | |
| 14.33.7 | 100% | 50% | 30% | Negative |
| 12.3.3 | 10% | 5% | 50% | N/D |
| MAb against subpopulations of SCS, BC and LC | | | | |
| 10.16.7 | <1% | <1% | Negative | 100% |
| 12.3.2 | 100% | 10% | 100% | 50% |

Analysis suggested MAb reactivity patterns with subpopulations of prostatic cells detected in normal prostate tissue and carcinoma specimens were preserved in cultured cells to a certain degree. Importantly, both large and small subpopulations of MAb reactive cells in tissue were present in cultures. To determine stability of the size of MAb reactive cell subsets during routine propagation at least two consecutive passages of all cultured cells were tested. PC-3 cells, an aggressive prostate cancer cell line, was studied for more then 10 passages including some of the clonal derivatives produced during the course of this investigation. Analysis indicated that large fractions of MAb reactive cells could increase or decrease. However, the negative fraction detected on the previous passage could be always identified. In contrast, minor subpopulations of the MAb reactive cells remained in small numbers from passage to passage. (Table 3). At low passages, phenotypic changes were minimal, but they increased significantly as the cells approached senescence. Overall, the combined data indicates close similarity of phenotypes and cellular compositions detected in normal tissue and in cultured cells.

TABLE 3

Phenotype of the primary normal adult prostate epithelial cells

| MAb clone | Pass 2 | Pass 3 | Pass 4 | Pass 5 |
|---|---|---|---|---|
| CK14 | 50% | 50% | 80% | 80–90% |
| CK8/18 | 90% | 100% | N/D | 100% |
| SCS7 (7.22.3) | <1% | 1–3% | 30% | 50–60% |
| 6.19.10 | <1% | 1–3% | 30% | N/D |
| SB6 (6.39.2) | 50% | 50% | N/D | N/D |
| 7.18.1 | N/D | 70% | 90% | N/D |
| 9.5.5 | 1–3% | 5% | 3–5% | N/D |
| 5.37.1 | 90% | 90% | N/D | N/D |
| 13.2.7 | 10% | 20% | N/D | 80% |
| SA7 (7.40.1) | 90% | <100% | N/D | N/D |
| 12.3.3 | <100% | <100% | N/D | N/D |

MAb clones showing strong reactivity with at least one of the cell lines were used to examine which of the specific epitopes were localized on the cell surface. IIF labeling of live cells in suspension showed by IIF microscopy examination that out of 37 selected MAbs, 22 strongly recognized surface antigens suggesting the potential use of this panel for immuno fractionation of antigenically defined subpopulations. All nine MAb selected, including those labeling minor subpopulations were also tested by FACS. MAb SCS7 was applied to isolate SCS7+ cells from PC-3 cells using immuno magnetic beads. Enriched to 97–99% SCS+ cells (total $1\times10^5$) were cultured at the same conditions as the parental cells. SCS7 enriched PC-3 cells were passaged 5 times and chamber slides were set at each passage to assess phenotype. Analysis indicated that SCS7+ cells produced SCS7 negative progeny from the very beginning and diminished in rate to 5% by the fifth passage. We previously determined by double label IF that MAbs SCS7, 9.5.5, 7.18.9 and 10.16.7 (cytoplasmic antigen) label separate subsets of cells in parental PC-3 cultures (Table 2). Thus if SCS7+ cells were PC-3 cells progenitors, as proposed, it was hoped the isolated cell type will differentiate into a phenotypically heterogeneous population resembling parental cells to indicate pluripotentiality of the initial cells. Indeed, in two separate experiments all of the small subsets were present in MAb SCS7 enriched cultures by passage 3.

Twenty SCS7+ PC-3 cells were cloned by limiting dilution and initiated data collection on phenotypes in these clones to get insight into differentiation potential of individual cells. Similar isolation of SCS7+ cells from normal primary PEC strain at passages 3 and 4 was also performed. Of the 8 separate cultures initiated from $1\times10^3$ cells in chamber slides and regular dishes two cultures slowly proliferated to 60% confluency and were fixed determine phenotype while other cultures senesced. Both of the expanded clones tested positive for CK14+ and 9.5.5+ cells but were primarily composed of SCS7+ cells to suggest only few of the isolated cells were growing and differentiating. Isolation at passage 4 resulted in cultures that were maintained for over 2 month without passaging. Cultured cells readily attached to the dish but did not proliferate while not senescing either. Overall, initial attempts to sufficiently expand the cultures over 2–3 passages and increase the total number of SCS7+ cells prior to isolation does not appear practical. Based on the obvious decrease in growth rate of the parental cultures at passage 3–4 and associated with notable phenotype changes (Table 3), it was presumed, that current cell culture conditions do not stably induce proliferation of SCS7+ cells but support their long term survival. We recently initiated improvements of the existing cell culture conditions by at first screening commercially available extracellular matrices Collagen I, IV, Laminin and ECM (ExtraCellular Matrix, Sigma) to support extended passaging of the normal PEC. Initial results suggest that at the present media conditions Collagen IV mixed with Laminin ECM could be beneficial to the cultures, a desired outcome that has to be further evaluated.

Some prostate-reactive monoclonal antibodies demonstrate antibody reactivity with mesodermally derived stem cells of the kidney, ureter, and seminal vesicle. These tissues represent some of the epithelial tissues that are derived from the Wollfian duct of the mesoderm.

Example 4

Patterns of MAb Reactivity with Human Prostate Tissue

MAb reactivity was evaluated in adult prostate tissues and immature cells of a developing human prostate. Tissues were collected at the 8th and 14th week of gestation. Whole mount transverse sections of the fetal pelvis were cryosectioned to produce serial sections. Every 5th section was stained and analyzed to provide topographical orientation and histological information. Sections containing tissues of urogenital sinus (UGS) at the 8th week or prostate primordia emerging from the UGS at 14th week were labeled by single or double label IIF with the MAbs described herein. Results of the labeling indicated that seven of 9 MAb clones tested were reactive with subpopulations of UGS cells at 8th week, and prostate or ejaculatory duct at 14th week. Identification of antigenically distinct cell populations within the urogenital sinus indicated that the SCS-reactive MAbs detected early stages in differentiation and/or lineage commitment of prostate epithelial cells. These data indicated the presence of progenitor or stem cells in the adult prostate.

The following MAb and PAb were used as reference cell type specific markers and controls: MAb and PAb against Cytokeratin (CK) 8/18 (Enzo Diagnostics) and PSA (polyclonal, Dako) for Luminal and Intermediate cells; CK14 (Clone LLOO1 (IgG) and CKBI (IgM) from Sigma, and MAb K903 cells were then incubated with appropriate dilutions of MAb for 45 min. on ice, cells were spun down, washed twice in phosphate buffered saline (PBS) to remove unbound MAb and labeled with fluorochrom conjugated secondary antibody for 30 min on ice. Following two washes in PBS cells were suspended in PBS and counterstained with Propidium Iodide to identify nonviable fraction and examined on FACScan (Becton Dickinson).

The proportion of cells grown in chamber slides stained with each MAb was determined by counting total number of cells under the phase contrast and a number of stained cells with IIF. Three fields per slide were analyzed. Immunofractionation of the SCS7+ cells using a standard immunobead enrichment technique to isolate rare circulating prostate cancer cells. The volume of cell-bead suspensions prior to cell separations in the magnetic field was increased 10 fold to minimize nonspecific binding of antigen negative cells to the beads and assure high purity of the bead bound fraction. These protocols were used to fractionate rat PEC using strongly reactive surface MAbs developed against liver oval cells.

Adult prostate tissues analyzed were as surgical specimens. As soon as tissue samples were obtained, they are rapidly frozen in a dry ice hexane bath. A large series of frozen sections were air dried, fixed in ice cold acetone and stored in sealed boxes at −80 C. The remainder of the frozen tissue was stored in a similar manner. Every 10th section was fixed in paraformaldehyde/methanol, stained with H&E and coverslipped.

Primary normal prostate epithelial cells were originated from a tissue specimen obtained by radical prostatectomy for unilateral and moderately differentiated prostate cancer. A portion of the prostate contralateral to the one containing cancer cells was used to establish cultures. Histological evaluation of the tissue sections adjacent to the area from which cultures were derived indicated absence of carcinoma foci. Minced tissues were further dissociated to single cells or small fragments in a HBSS buffer solution supplemented with 0.025 MM CaCl2, 0.1% BSA (Sigma), 0.1% Collagenase Type 1 (158 units/mg, Gibco BRL), 0.1% protease Type XIV (5.3 units/mg, Sigma) and incubated in a shaking water bath for 1 hr at 37° C. Digestion was stopped by two washes with RPMI 1640 media containing 5% Fetal Bovine Serum (FBS). After settling at 1×g for 5 min, the supernatant containing single cells, was removed and the undigested tissue fragments were dissociated at 37° C. in 10 ml Dispase digestion media (Collaborative Biomed. Products) for 30 min. with agitation. Dissociation was terminated by addition of an equal volume of RPMI 1640 media supplemented with 5% FBS. Cell cultures were initiated in plastic dishes at high density and in minimal amount of media. Media was composed of a 1:1 mixture of RPMI 1640/MCDB 153 supplemented with 2–3% charcoal stripped heat inactivated fetal bovine serum and commercial preparations of growth factors: EGF 20 ng/ml, cholera toxin 20 ng/ml, dexamethesone 10 mM, ITS (Insulin, Transferrin, Selenous acid) 10 ng/ml, BPE (Bovine Pituitary Extract) 20 ng/ml. 5 to 7 days after culture initiation, when expanding colonies become apparent concentration of the growth factors was reduced by half and maintained at this level in all studies. This formulation supports the growth of epithelial cells at the expense of stromal cells. One of the established cell strains was found to be nontumorigenic when injected subcutaneously into SCID mice for a period of 4 months. Epithelial origin was established by negative reactivity with Desmin, and Factor VIII MAbs and positive reactivity with CK 8/18 and CK 14 MAbs, a basal cell marker down-regulated in primary carcinoma strains. Cultured cells tested negative for PSA. Established normal PEC strain was also tested at passage 3 for the ability to grow and differentiate when recombined with rat UGS mesenchymal cells and grafted beneath the kidney capsule of male athymic nude mice.

Example 5

Immuno-enrichment of SCS7+ Cells from Prostate Derived Cell Lines

Initial screening of MAbs on frozen prostate tissues suggested significant differences in patterns of reactivity displayed by normal prostate tissues and carcinomas. MAbs have been identified showing consistent reactivity with subpopulations of PEC in the peripheral zone of normal prostate. MAb reactive cells in normal prostate were subdivided into four types: luminal cells (LPEC) in direct contact with the glandular lumen; intermediate cells located above the basal and underneath the luminal cells; basally located cells (BPEC) that were directly adjacent to the basal membrane, separating them from the stromal compartment but with no direct contact with the lumen; and a very small population of MAb reactive cells located in the stroma with the majority in close proximity to the basal membrane. Among the 37 antibodies selected for further analysis, seven showed consistent reactivity with the small subset of single cells in stroma ("SCS") in normal prostate. Epitopes/antigens recognized by these 7 MAbs were either exclusively expressed by SCS or shared with subpopulations of glandular PEC. Among the 7 antibodies reactive with surface epitopes on SCS in normal prostate, three hybridomas producing antibodies with strongest reactivity for SCS and primary carcinomas (MAb SCS7, SA7 and SB6) were selected for further characterization.

To determine if MAb SCS7 could be used for immunoenrichment of normal or prostate carcinoma cells, cultured cells from the PC-3 cell line which had been incubated with MAb SCS7 were mixed with the magnetic Dynabeads covalently coated with goat anti mouse Ig antibodies. Bead-bound, antigen positive cells were subsequently separated from negative cells in a magnetic field. Prior to enrichment, IIF analysis showed that less than 1% of cells in PC-3 cultures and PC-3 tumor nodules grown in SCID mice were positive for SCS7. IIF staining of cytospins prepared from the bead bound cells immediately after immunobead isolation indicated the percentage of positive cells had been increased to approximately 98%.

SCS7− cells began to appear in cultures after the first passage. This SCS7− population also acquired the expression of several other markers for which the initial SCS7+ population was negative. After several passages, the SCS7+ cells had diminished in numbers and reached a steady state level of 5% of the total cell population. These findings indicated that the SCS7+ cells had undergone a further step in differentiation that resulted in the loss of SCS7 and the acquisition of additional markers associated with other prostate epithelial cells. Alternatively, the apparent loss of SCS7+ cells could have resulted from the overgrowth of the cultures by a small population of contaminating negative cells which possessed a significantly higher rate of proliferation than their positive counterparts.

To determine the feasibility of isolating MAb SCS7+cells from primary PEC cells and/or directly from prostate tissues, an immunomagnetic enrichment of cultured normal PEC using the same bead enrichment protocol described for PC-3 carcinoma cells was performed. A primary PEC cell line from a tissue specimen obtained by radical prostatectomy for unilateral and moderately differentiated prostate cancer was obtained. A portion of the prostate contralateral to the one containing cancer cells was used to establish cultures. Histological evaluation of the tissue sections adjacent to the area from which cultures were derived indicated the absence of carcinoma foci. Phenotypic analysis of the resulting cultures using established epithelium specific markers confirmed their epithelial origin and demonstrated a strong reactivity of a large cell subset with anti-CK14 MAbs, a basal cell marker downregulated in primary carcinoma strains. Long term propagation of these cells showed decrease in growth rate resulting in senescence at passage 9 or after 4 months. These cells were also found to be nontumorigenic when injected subcutaneously into immunodeficient mice. Immuno-fractionation of the SCS7+primary PEC at passage 3 was successful and produced 98–99% pure isolates as determined by the SCS7+/CK14- phenotype.

Prior to isolation, SCS7+ cells in this cell line were detected at a 0.5–1% level in the total cell population with a few cells co-expressing both CK14 and SCS7. Doubly positive cells in primary cultures with a phenotype intermediate between SCS and basal cell were consistent with the in situ IIF findings. Bead-bound SCS7+ cells expanded in culture demonstrated phenotypic changes similar to SCS7+ PC-3 carcinoma cells. After two passages, the SCS7+ cell population decreased to 1–2% and the majority of the new and actively proliferating cells displayed an SCS7−/CK14+ phenotype. This data confirmed the reproducibility of the immunobead enrichment protocols for fractionating primary PEC using MAb directed against prostate stem cells and further demonstrated the usefulness of an immunoseparation approach to isolate stem cells and assess the ongoing process of differentiation.

Other Embodiments

Although particular embodiments have been disclosed herein in detail, this has been done by way of example for purposes of illustration only, and is not intended to be limiting with respect to the scope of the appended claims that follow. In particular, it is contemplated by the inventor that various substitutions, alterations, and modifications may be made to the invention without departing from the spirit and scope of the invention as defined by the claims. For example, the selection of the specific tissue(s) or cell line(s) that is to be utilized in the practice of the present invention is believed to be a matter of routine for a person of ordinary skill in the art with knowledge of the embodiments described herein.

What is claimed is:

1. An isolated monoclonal antibody produced by a hybridoma deposited with the American Type Culture Collection as Accession No. PTA-4655, or an antigen-binding fragment thereof.

2. The isolated antibody, or antigen-binding fragment thereof, of claim 1, wherein the antigen-binding fragment thereof is selected from the group consisting of an $F_{ab}$ fragment, an $F_{(ab')2}$ fragment, and an Fv fragment.

3. The isolated antibody or antigen-binding fragment thereof of claim 1, wherein the isolated antibody, or antigen-binding fragment thereof, is coupled with a detectable substance.

4. The isolated antibody, or antigen-binding fragment thereof, of claim 3, wherein the detectable substance is selected from the group consisting of enzymes, prosthetic groups, fluorescent materials, luminescent materials, bioluminescent materials, and radioactive materials.

5. The isolated antibody, or antigen-binding fragment thereof, of claim 4, wherein the enzyme is selected from the group consisting of horseradish peroxidase, alkaline phosphatase, β-galactosidase, and acetylcholinesterase.

6. The isolated antibody, or antigen-binding fragment thereof, of claim 4, wherein the prosthetic group is selected from the group consisting of streptavidin, biotin, and avidin.

7. The isolated antibody, or antigen-binding fragment thereof, of claim 4, wherein the fluorescent material is selected from the group consisting of umbelliferone, fluorescein, fluorescein isothiocyanate, rhodamine, dichlorotriazinylamine fluorescein, dansyl chloride, and phycoerythrin.

8. The isolated antibody, or antigen-binding fragment thereof, of claim 4, wherein the luminescent material is luminol.

9. The isolated antibody, or antigen-binding fragment thereof, of claim 4, wherein the bioluminescent material is selected from the group consisting of luciferase, luciferin, and aequorin.

10. The isolated antibody, or antigen-binding fragment thereof, of claim 4, wherein the radioactive material is selected from the group consisting of $^{125}I$, $^{131}I$, $^{35}S$, and $^3H$.

11. The isolated antibody, or antigen-binding fragment thereof, of claim 1, wherein the isolated antibody, or antigen-binding fragment thereof, is coupled with a cytotoxic agent.

12. A diagnostic kit comprising the isolated antibody, or antigen-binding fragment thereof, of claim 1.

13. A diagnostic kit comprising the isolated antibody, or antigen-binding fragment thereof, of claim 2.

14. A diagnostic kit comprising the isolated antibody, or antigen-binding fragment thereof, of claim 5.

15. An isolated recombinant antibody, or an antigen-binding fragment thereof, comprising all antigen binding specificities of an antibody produced by a hybridoma deposited with the American Type Culture Collection as Accession No. PTA-4655.

16. The isolated recombinant antibody, or an antigen-binding fragment thereof, of claim 15, wherein the recombinant antibody is a chimeric antibody or a humanized antibody.

17. A diagnostic kit comprising the isolated antibody, or antigen-binding fragment thereof, of claim 15.

18. A diagnostic kit comprising the isolated antibody, or antigen-binding fragment thereof, of claim 16.

* * * * *